United States Patent
Bentz et al.

(10) Patent No.: US 11,116,445 B2
(45) Date of Patent: Sep. 14, 2021

(54) METHODS FOR LOCATING DISCONTINUITIES IN TISSUE USING OPTICAL IMAGING, SURGICAL PROCEDURES, AND DEVICES FOR USE DURING SURGICAL PROCEDURES

(71) Applicant: PURDUE RESEARCH FOUNDATION, West Lafayette, IN (US)

(72) Inventors: Brian Zahler Bentz, West Lafayette, IN (US); Kevin John Webb, West Lafayette, IN (US); Timothy Cheng-Hsien Wu, San Mateo, CA (US); Vaibhav Gaind, Fremont, CA (US)

(73) Assignee: Purdue Research Foundation, West Lafayette, IN (US)

( * ) Notice: Subject to any disclaimer, the term of this patent is extended or adjusted under 35 U.S.C. 154(b) by 576 days.

(21) Appl. No.: 15/975,211

(22) Filed: May 9, 2018

(65) Prior Publication Data
US 2018/0325449 A1 Nov. 15, 2018

Related U.S. Application Data

(60) Provisional application No. 62/503,410, filed on May 9, 2017.

(51) Int. Cl.
*G06T 7/00* (2017.01)
*A61B 5/00* (2006.01)
*A61B 1/04* (2006.01)

(52) U.S. Cl.
CPC ............ *A61B 5/489* (2013.01); *A61B 5/0077* (2013.01); *A61B 1/043* (2013.01); *A61B 5/0059* (2013.01);

(Continued)

(58) Field of Classification Search
CPC ....... A61B 5/489; A61B 5/0077; A61B 1/043; A61B 5/0059; G06T 7/0012; G06T 2207/30101
See application file for complete search history.

(56) References Cited

U.S. PATENT DOCUMENTS

| 8,464,710 B1 * | 6/2013 | Franckowiak .... A61M 16/0488 |
| | | 128/200.26 |
| 2001/0053510 A1 * | 12/2001 | Ranalli ................. A61C 19/04 |
| | | 433/51 |

(Continued)

OTHER PUBLICATIONS

Van de Ven et al. A Novel Fluorescent Imaging Agent for Diffuse Optical Tomography of the Breast: First Clinical Experience in Patients. Mol Imaging Biol 12, 343-348 (2010). https://doi.org/10.1007/s11307-009-0269-1 (Year: 2010).*

(Continued)

*Primary Examiner* — Amanda Lauritzen Moher
*Assistant Examiner* — Jillian K. McGough
(74) *Attorney, Agent, or Firm* — Hartman Global IP Law; Gary M. Hartman; Domenica N. S. Hartman

(57) ABSTRACT

Methods for locating blood vessels, lesions, and other discontinuities in tissue such as, but not limited to, the greater palatine artery (GPA) in the hard palate using an optical imaging process, surgical procedures utilizing the identified locations of discontinuities, and devices suitable for use during surgical procedures. According to one aspect, such a method locates a blood vessel or lesion in tissue by imaging the tissue via a diffuse optical imaging (DOI) process that measures light that travels through the tissue, and then locates the blood vessel or lesion in the tissue based on a difference in absorption of the light between the tissue and the blood vessel or lesion.

12 Claims, 7 Drawing Sheets
(2 of 7 Drawing Sheet(s) Filed in Color)

(52) U.S. Cl.
CPC .. *G06T 7/0012* (2013.01); *G06T 2207/30101* (2013.01)

(56) References Cited

U.S. PATENT DOCUMENTS

| | | | | |
|---|---|---|---|---|
| 2002/0151975 | A1* | 10/2002 | Farr, II | A61B 17/1675 623/14.12 |
| 2009/0011382 | A1* | 1/2009 | Bavar | A61C 1/084 433/76 |
| 2009/0081618 | A1* | 3/2009 | LaMar | A61C 8/0069 433/218 |
| 2011/0129792 | A1* | 6/2011 | Berckmans, III | A61C 8/005 433/72 |
| 2016/0331472 | A1* | 11/2016 | Dayan | A61B 17/3468 |

OTHER PUBLICATIONS

Frisardi et al. "Integration of 3D anatomical data obtained by CT imaging and 3D optical scanning for computer aided implant surgery". BMC Medical Imaging 2011, 11:5. http://www.biomedcentral.com/1471-2342/11/5 (Year: 2011).*

McLaughlin et al. "Side-Cutting Aspiration Device for Endoscopic and Microscopic Tumor Removal". Journal of Neurological Surgery—Part B vol. 73 No. B1/2012 . http://dx.doi.org/10.1055/s-0032-1304834 (Year: 2012).*

Singh et al. "Optical coherence tomography for image-guided dermal filler injection and biomechanical evaluation," Proc. SPIE 10037, Photonics in Dermatology and Plastic Surgery, 100370W (Feb. 6, 2017); doi: 10.1117/12.2251541 . (Year: 2017).*

Bentz et al. "3D printed optical phantoms and deep tissue imaging for in vivo applications including oral surgery," Proc. SPIE 10056, Design and Quality for Biomedical Technologies X, 1005607 (Mar. 14, 2017); doi: 10.1117/12.2253763. (Year: 2017).*

Balasundaram et al. "Novel CBCT and Optical Scanner-Based Implant Treatment Planning Using a Stereolithographic Surgical Guide: A Multipronged Diagnostic Approach ". Implant Dentistry/ vol. 23, No. 4 2014. (Year: 2014).*

Patachia et al. "Blood oxygenation monitoring by diffuse optical tomography". 2010 Quantum Electron. 40 1062 (Year: 2010).*

Lee et al. "Accuracy of a direct drill-guiding system with minimal tolerance of surgical instruments used for implant surgery: a prospective clinical study". J Adv Prosthodont 2016;8:207-13. (Year: 2016).*

A.P. Gibson, J.C. Hebden, and S. R. Arridge, "Recent advances in diffuse optical imaging", Phys. Med. Biol. 50, R1 (2005).

K. K. Tremper, "Pulse oximetry", Chest 95, 713-715 (1989).

S. R. Arridge, "Optical tomography in medical imaging", Inverse Prob. 15, R41-R93 (1999).

J. C. Ye, K. J. Webb, C. A. Bouman, and R. P. Millane, "Optical diffusion tomography using iterative coordinate descent optimization in a Bayesian framework", J. Opt.Soc.Am. A 16, 2400-2412 (1999).

A. B. Milstein, M. D. Kennedy, P.S. Low, C. A. Bouman, and K. J. Webb, "Statistical approach for detection and localization of a fluorescing mouse tumor in Intralipid", Appl. Opt. 44, 2300-2310 (2005).

G. Cao, V. Gaind, C.A. Bouman, and K. J. Webb, "Localization of an absorbing inhomeogeneity in a scattering medium in a statistical framework", Opt. Lett. 32, 3026-3028 (2007).

S.K. Klosek and T. Rungruang, "Anatomical study of the greater palatine artery and related structures of the palatal vault: considerations for palate as the subepithelial connective tissue graft donor site", Surg. Radiol. Anat. 31, 245-250 (2009).

K. H. Cho, S.K. Yu,M.H. Lee, D.S. Lee, and H.J. Kim, "Histologial assessment of the palatal mucosa and grater palatine artery with reference to subepithelial connective grafting", Anat.Cell Bio. 46, 171-176 (2013).

A. Roggan, M. Friebel, K. Dorschel, A. Hahn, and G. Muller, "Optical properties of circulating human blood in the wavelength range 400-2500 nm", J. Biomed. Opt 4, 36-46 (1999).

J. Ye, K. Webb, R.Millane and T. Downar, "Modified distorted Born iterative method with an approximate Frechet derivative for opticaldiffusion tomography", J. Opt.Soc. Am. A 16, 1814-1826 (1999).

M. Schweiger and S.Arridge, "The Toast++ software suite for forward and inverse modeling in optical tomography", J. biomed. Opt. 19, 040801-040801 (2014).

B. Z. Bentz, A. V. Chavan, D. Lin, E. H. Tsai, and K. J. Webb, "Fabrication and application of heterogeneous printed mouse phantoms for whole animal optical imaging", Appl. Opt. 55, 280-287 (2016).

B. Z. Bentz, A G. Bowen, D. Lin, D. Ysselstein, D. H. Huston, J.-C. Rochet, and K. J. Webb, "Printed optics: phantoms for quantitative deep tissue fluorescense imaging", Opt. Lett. 41, 5230-5233 (2016).

P. Di Ninni, F. Martelli, and G. Accanti, "The use of India ink in tissue simulating phantoms", Opt. Exp. 18, 26854-26865 (2010).

B. Z. Bentz, A. Costas, V. Gaind, J. M. Garcia, and K. J. Webb, "3D printed optical phantoms and deep tissue imaging for in vivo applications including oral surgery", SPIE BiOS 10056, 1005607 (2017).

K. M. D'Souza and M. A. Aras, "Types of implant surgical guides in dentistry: a review", J. Oral Implantol. 38, 643-652 (2012).

D. P. Sarment, P. Sukovic, and N.Clinthorne, "Accuracy of implant placement with a sterolithographic surgical guide", Int. J. Oral Maxillofac. Implants 18 (2013).

* cited by examiner

METHODS FOR LOCATING DISCONTINUITIES IN TISSUE USING OPTICAL IMAGING, SURGICAL PROCEDURES, AND DEVICES FOR USE DURING SURGICAL PROCEDURES

CROSS REFERENCE TO RELATED APPLICATIONS

This application claims the benefit of U.S. Provisional Application No. 62/503,410, filed May 9, 2017, the contents of which are incorporated herein by reference.

STATEMENT REGARDING FEDERALLY SPONSORED RESEARCH

This invention was made with government support under the Contract No. CA 182235 awarded by the National Institute of health. The government has certain rights in the invention.

BACKGROUND OF THE INVENTION

The present invention generally relates to locating blood vessels, lesions, and other discontinuities in tissue using light. The invention particularly relates to systems and methods for locating the greater palatine artery (GPA) in the hard palate to assist in oral surgery and devices for use during oral surgery.

The GPA is an anatomical landmark for oral surgery. The depth of the GPA varies in humans, but it is generally located at a depth of about five millimeters into the roof of a human mouth, and is not visible with the naked eye. It has an approximate length of about 39 mm, and its outer diameter (which varies along its length) is generally about 2.65 mm. Along with the greater palatine nerve (GPN), it forms the greater palatine neurovascular bundle (GPB), which emerges from the pterygopalatine fossa through the greater palatine foramen and runs anteriorly and anastomoses with branches of the nasopalatine bundle from the nasopalatine canal. The location of the GPB is associated with the height of the palatal vault, ranging from 7 to 17 mm from the cementoenamel junctions of the maxillary premolars and molars. Currently, a surgeon must rely on prior knowledge of the GPA location to avoid damaging it or the GPN during oral surgery. However, a recent study with human cadavers showed a discrepancy in the location of the GPB of up to 4 mm. This lack of exact knowledge of the GPA location may cause complications during periodontal and oral surgeries, sinus and ridge augmentations, GPN block, soft tissue biopsies, dental implant, and wisdom teeth removal.

A potential serious complication of oral surgery involving the hard palate is hemorrhage. Significant arterial bleeding can occur if the GPA is severed, especially if this occurs close to the greater palatine foramen, as the artery may retract into the bony canal making it difficult to access for ligation, pressure, and the usual surgical approaches for rapid control of hemorrhage. Most surgeons, therefore, justifiably avoid involving the entire range of possible locations of the greater palatine canal and surrounding area in the surgical field. However, this can result in compromised surgical design. Certain oral surgical procedures involve the harvest of soft tissue from the hard palate, for example, as the donor site for gingival grafting procedures performed by periodontists. Soft tissue from the hard palate is also harvested as autologous donor tissue in ophthalmologic reconstruction surgery. The limiting factor in grafting is the amount of donor tissue available. If the exact location of the artery was known a potentially larger surface area would be available for harvesting, thus increasing the amount of available donor tissue during a given surgical procedure. This would reduce and possibly avoid the need for additional follow-up surgery after regrowth of tissue at the donor site, for example, in cases where multiple teeth need gingival grafting. Similarly, inadequate reflection of palatal flaps in attempts to avoid the palatine artery in ridge augmentation procedures, implant placement, or periodontal and other oral surgery can cause compromised results.

Anatomic and radiographic studies of the greater palatine foramen location in different populations continue to be published in peer-reviewed journals with the goal of identifying landmarks to predict its location during surgical procedures. This demonstrates the continued interest and concerns of surgeons when operating in this anatomic location. However, due to significant individual variation, these landmarks only provide a rough estimate of the actual location in a given patient. At present there is no available means to accurately identify the location of the foramen and artery in an individual patient in real time during surgery, and is therefore an unmet clinical need.

In view of the above, it can be appreciated that it would be desirable if systems and/or methods were available for localization of the GPA in a patient. Furthermore, in general, it would be desirable to promote the ability to locate blood vessels, lesions, and other discontinuities within tissue during surgery to improve surgical design and outcomes.

BRIEF DESCRIPTION OF THE INVENTION

The present invention provides methods for locating blood vessels, lesions, and other discontinuities in tissue such as, but not limited to, the GPA in the hard palate, using an optical imaging process, surgical procedures utilizing the identified locations of blood vessels, lesions, and other discontinuities, and devices suitable for use during surgical procedures.

According to one aspect of the invention, a method is provided for locating a blood vessel or lesion in tissue that includes imaging the tissue via an optical imaging process that measures light that travels through the tissue, and then locating the blood vessel or lesion in the tissue based on a difference in absorption or scattering of the light between the tissue and the blood vessel or lesion.

According to another aspect of the invention, an oral surgery procedure includes imaging the hard palate via an optical imaging process that measures light that travels through the hard palate, locating the greater palatine artery (GPA) in the hard palate based on a difference in absorption of the light between the GPA and surrounding soft tissue in the hard palate, and then operating on the hard palate while avoiding the location of the GPA.

According to another aspect of the invention, a device is provided that includes a body configured to be secured in the mouth. When secured in the mouth, the body masks portions of the hard palate corresponding to the location of the greater palatine neurovascular bundle (GPB) and thereby reduces the likelihood that the GPB will be damaged when performing an oral surgery procedure on the hard palate.

Technical effects of the procedures and devices described above preferably include the ability to perform a surgical procedure on a living body with a significantly reduced likelihood that a blood vessel will be damaged, or alternatively, with the ability to facilitate the removal of a lesion.

Other aspects and advantages of this invention will be further appreciated from the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
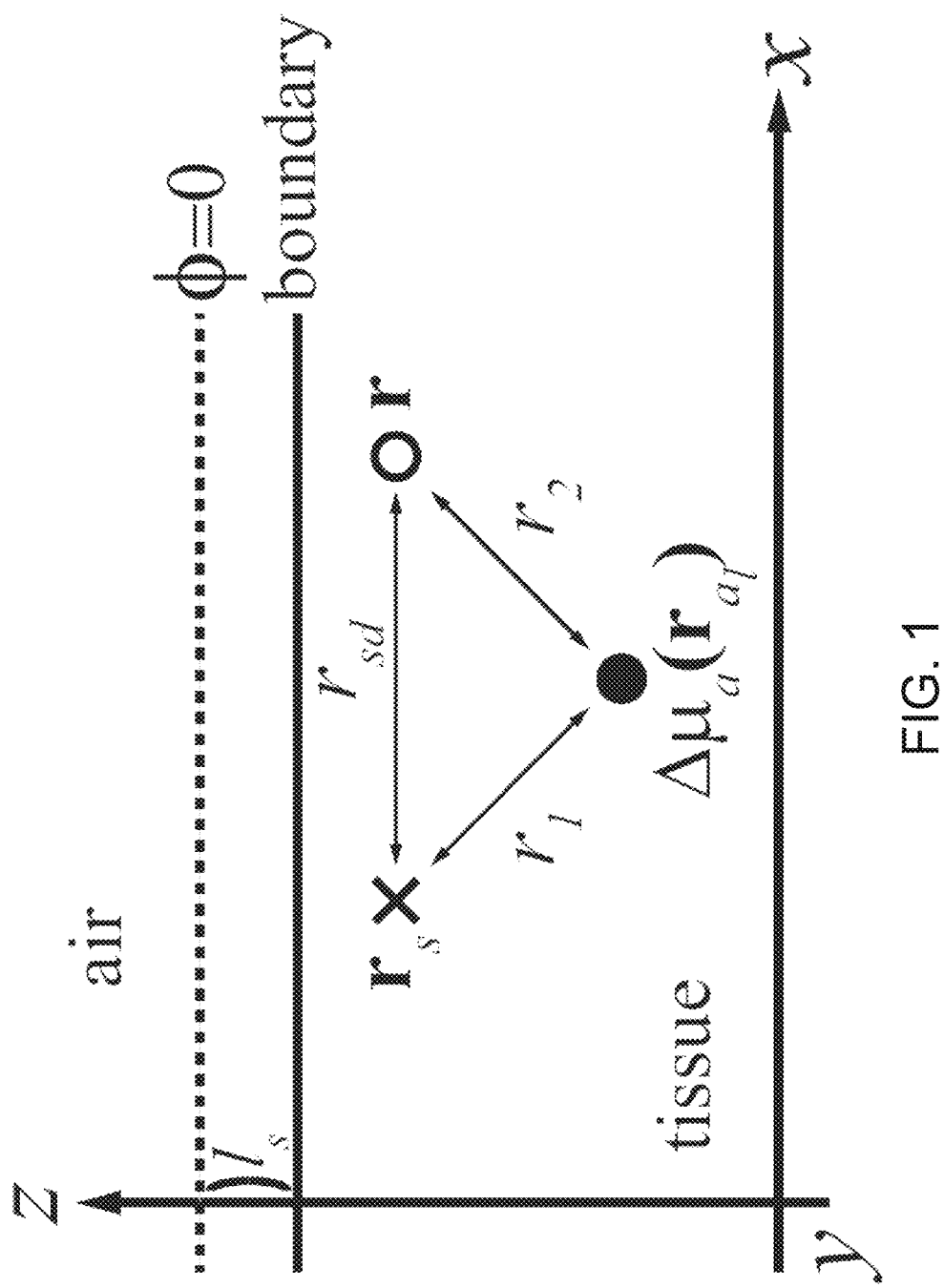
FIG. 1 is a plot representing a reflection measurement geometry that may be considered as a nonlimiting localization geometry in reference to nonlimiting aspects of the invention.

This disclosure provides systems and methods for locating blood vessels, lesions, and other discontinuities, in a body and using this localization information to improve or assist in surgical procedures. For convenience, aspects of the invention are discussed herein in reference to a nonlimiting embodiment in which the greater palatine artery (GPA) in the roof (palate) of a human mouth is located to assist in oral surgery performed on a human patient, though other uses exist (including various procedures that might be performed on humans, nonhuman living creatures, and inanimate objects). The invention will also be discussed in reference to devices for use during oral surgery, as well as various other procedures as noted above.

According to preferred aspects of the invention, the GPA may be located using localization methods that rely on optical imaging and, once the GPA has been located, such localization information may optionally be used to produce a guide for surgical procedures, including but not limited to periodontal and oral surgeries, sinus and ridge augmentations, GPN block, soft tissue biopsies, dental implant, wisdom teeth removal, and harvesting of donor tissue. However, it should be understood that the general concepts of the invention are applicable to various other procedures, treatments, and subjects, including inanimate objects and living creatures other than humans. In addition, equations disclosed herein are exemplary and are based on assumptions used during investigations leading to certain aspects of the present invention. It is foreseeable and within the scope of the invention that such equations may be modified and/or other equations and assumptions may be used.

Diffuse optical imaging (DOI) is the extraction of information from measurements of light that has traveled through scattering media such as tissue. Instrumentation for DOI is typically inexpensive and safe, and related technology has been used to develop highly successful pulse oximetry devices. In DOI methods such as diffuse optical tomography (DOT), near infrared or visible light is used to form volumetric images in deep (>1 cm) tissue by treating photons as diffusing particles. However, this is a computationally intensive process, limiting its application in surgery where information is often needed in real time. For this reason, fast localization methods are an attractive alternative, where information about the location only is extracted.

DOI can be implemented using a model of light transport in tissue. The diffusion approximation to the radiative transport equation has been shown to be appropriate, and is presented here. The optical parameters of interest in the diffusion model are the absorption coefficient $\mu_a$ and the reduced scattering coefficient $\mu'_s$. These parameters characterize a diffusion equation that describes the propagation of light within a highly scattering medium. For an unmodulated or continuous wave (CW) light source, the diffusion equation reduces to $$\nabla \cdot [D(r)\nabla\phi(r)] - \mu_a(r)\phi(r) = \delta(r-r_s), \quad (1)$$

where r denotes the position, $\phi$ (W/mm$^2$) is the photon flux density, $D=1/[\mu'_s+\mu_a]$ (mm) is the diffusion coefficient, and a Dirac delta function excitation at position $r_s$ is assumed.

Localization of blood vessels such as the GPA in a human is possible because the absorption coefficient of the blood in the GPA is higher than the background tissue. The problem then becomes the estimation of the position of an absorption inhomogeneity. Previously, Cao et al., "Localization of an absorbing inhomogeneity in a scattering medium in a statistical framework," Opt. Lett. 32, 3026-3028 (2007), described localization of a single point absorber. In contrast, the present invention generally extends this treatment to the localization of multiple point absorbers or an absorption inhomogeneity of an arbitrary shape.

It can be assumed that the inhomogeneity is embedded in a locally homogeneous background having absorption coefficient ($\mu_{a_o}$) and diffusion coefficient ($D_o$) as known parameters, such that $\mu_a(r)=\mu_{a_o}+\Delta\mu_a(r)$, where $\Delta\mu_a$ is a perturbation in the absorption due to the inhomogeneity. After substitution into Eq. (1), moving the $\Delta\mu_a$ term to the right-hand side, assuming that $D(r)\approx D_o$ (since $\mu'_s \gg \mu_a$), and applying the Born approximation, the photon flux can be written as $$\phi(r;\Delta\mu_a)=\phi_i(r;\mu_{a_o})+\int dr'^3 g(r,r';\mu_{a_o})\phi_i(r';\mu_{a_o})\Delta\mu_a(r'), \quad (2)$$

where $\phi_i$ is the photon flux in a homogeneous background and $g(r, r'; \mu_{a_o})$ is the Green's function for the homogeneous diffusion equation with source location r'. In order to form an analytical solution for fast computation, it can be assumed that the inhomogeneity has constant $\Delta\mu_a$ and can be represented by L point absorbers at positions $r_{a_l}$ such that $$\phi(r;\Delta\mu_a) = \phi_i(r;\mu_{a_o}) + \Delta\mu_a \sum_{l=1}^{L} g(r,r';\mu_{a_o})\phi_i(r';\mu_{a_o})\Delta\mu_a(r'). \quad (3)$$

The forward model for a measurement at position r can then be written as $$f(R_a;\Delta\mu_a)=y_o+\Delta\mu_a f'(R_a), \quad (4)$$

where $$y_0 = \phi_i(r; \mu_{a_o}), \quad f'(R_a) = \sum_{l=1}^{L} g(r, r'; \mu_{a_o})\phi_i(r'; \mu_{a_o})\Delta\mu_a(r'),$$

and $R_a$ contains the L positions $r_{a_l}$. Equation (4) is nonlimiting, and the assumptions made in its derivation may be removed or modified.

The maximum likelihood (ML) estimate of the positions describing the inhomogeneity, $R_a$, can be formulated as the minimization of the cost function $$C(R_a) = \min_{\Delta\mu_a} \|y - y_o - \Delta\mu_a f'(R_a)\|_\Lambda^2, \quad (5)$$

where y is a vector of N measurements, $y_o$ is a vector of N expected measurements $y_o$, $f'(R_a)$ is a vector of N expected $f'(R_a)$, $\Lambda = \alpha \text{diag}[|y_1|, \ldots, |y_N|]$ is the noise covariance matrix, for which we assume a shot noise model characterized by $\alpha$, and for an arbitrary vector v, $\|v\|_\Lambda^2 = v^H \Lambda v$, where H denotes the Hermitian transpose. $\Delta\mu_a f'(R_a) = F'(R_a)\Delta\mu_a$, where $F'(R_a)$ is a compact Fréchet derivative matrix, which relates perturbations in the absorption image $\Delta\mu_a$ (a vector of length L) to the predicted measurement.

A two-step procedure can be used to solve this optimization problem, where for each combination of positions $r_{a_l}$ within a region of interest $$\Delta\tilde{\mu}_a(R_a) = \frac{Re[(y - y_o)^H \Lambda f'(R_a)]}{\|f'(R_a)\|_\Lambda^2}, \quad (6)$$

$$C(R_a) = \|y - y_o - \Delta\tilde{\mu}_a(R_a)f'(R_a)\|_\Lambda^2, \quad (7)$$

are calculated, and then the ML estimate is $$\hat{R}_a = \min_{R_a} C(R_a), \quad (8)$$

$$\Delta\hat{\mu}_a = \Delta\tilde{\mu}_a(\hat{R}_a). \quad (9)$$

In practice, constraints are required in order to reduce the complexity of the minimization. Because $\hat{R}_a$ is the parameter of interest, all linear dependencies in the problem can be encapsulated in $\Delta\tilde{\mu}_a$, including the excitation power, Green's function scalars, source-detector coupling into the medium, and the system parameter $\alpha$.

FIG. 1 schematically represents a reflection measurement geometry that may be considered as a nonlimiting localization geometry for a single point absorber (●) used to derive a forward model. An isotropic excitation source (X) and detector (○) at position r are placed one scattering length $l^* = 3D_o$ below a boundary. In a typical experiment, there are multiple sources and detectors resulting in N measurements. An analytic solution to Eq. (3) in an infinite domain leads to $$y_o = \frac{\exp(-kr_{sd})}{r_{sd}}, \quad (10)$$

$$f'(R_a) = \sum_{l=1}^{L} \left[\frac{\exp(-kr_{1_l})}{r_1}\right]\left[\frac{\exp(-kr_{2_l})}{r_2}\right], \quad (11)$$

where $k = \sqrt{\mu_{a_o}/D_o}$, $r_{1_l}$ is the distance from the excitation source to the lth point absorber, and $r_{2_l}$ is the distance from the lth point absorber to the detector.

Nonlimiting embodiments of the invention will now be described in reference to experimental investigations leading up to the invention.

To evaluate the approach discussed above in reference to FIG. 1 for the localization of the GPA, a mouth phantom was fabricated using the Form 1+3D printer commercially available from Formlabs, Inc. The phantom was printed using a standard white photopolymer resin also commercially available from Formlabs. By printing a slab of material and fitting experimental time-gated measurements to the analytical transmittance, the $\mu_{a_o}$ and $D_o$ of the printed material was measured at 633 nm to be 0.0076 mm$^{-1}$ and 0.166 mm, respectively. It was difficult to compare these values to the actual tissue because it was believed that $\mu_{a_o}$ and $D_o$ had not been measured for bulk gingival tissue. However, these values are similar to those for other tissues such as breast and brain. If the $\mu_{a_o}$ and $D_o$ of gingival tissue were known, the printed phantom could be designed to have the same values.

Figure 2B:
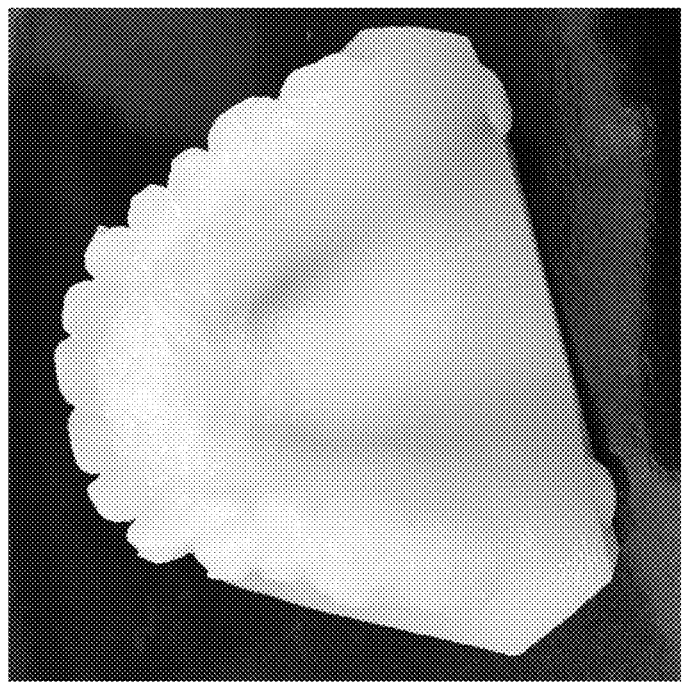
FIG. 2(b) is an image showing a phantom printed using the profile of FIG. 2(a), wherein the phantom includes absorbing inhomogeneities simulating the GPA.
Figure 2A:
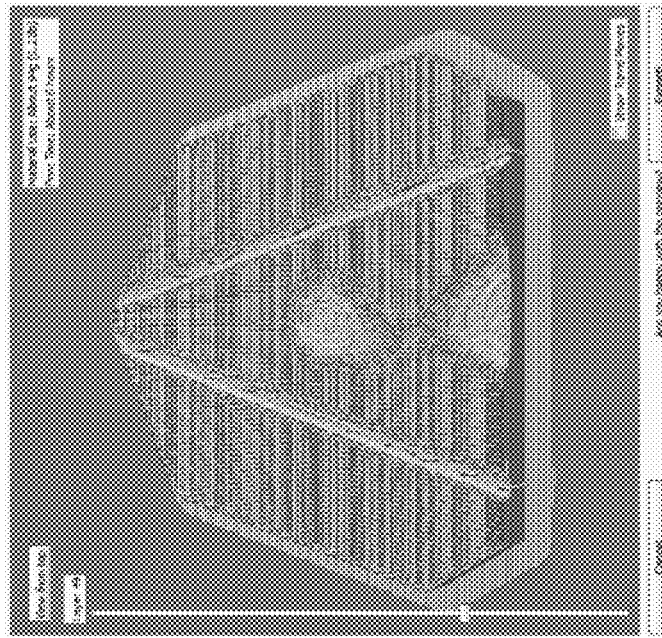
FIG. 2(a) is an image showing a slice of a printing profile and planar cylindrical cavities in the general location of the GPA within the hard palate of a human.

The phantom was designed with planar cylindrical cavities of diameter 2.65 mm to simulate a typical GPA, as shown in FIG. 2(a). The cavities were filled with a mixture of water and India ink (Higgins, 0.0018 (g/mL) density), simulating the absorption of blood at 633 nm, which is 0.7 mm$^{-1}$ for a 40% hematocrit level. FIG. 2(b) shows the resulting 3D printed mouth phantom. Visual inspection of the phantom shown in FIG. 2(b) suggested that $\mu_{a_o}$ of the phantom was less than gum tissue since the absorption inhomogeneities were visible under room light. However, the phantom was still useful for development of the localization approach described herein.

Figure 3:
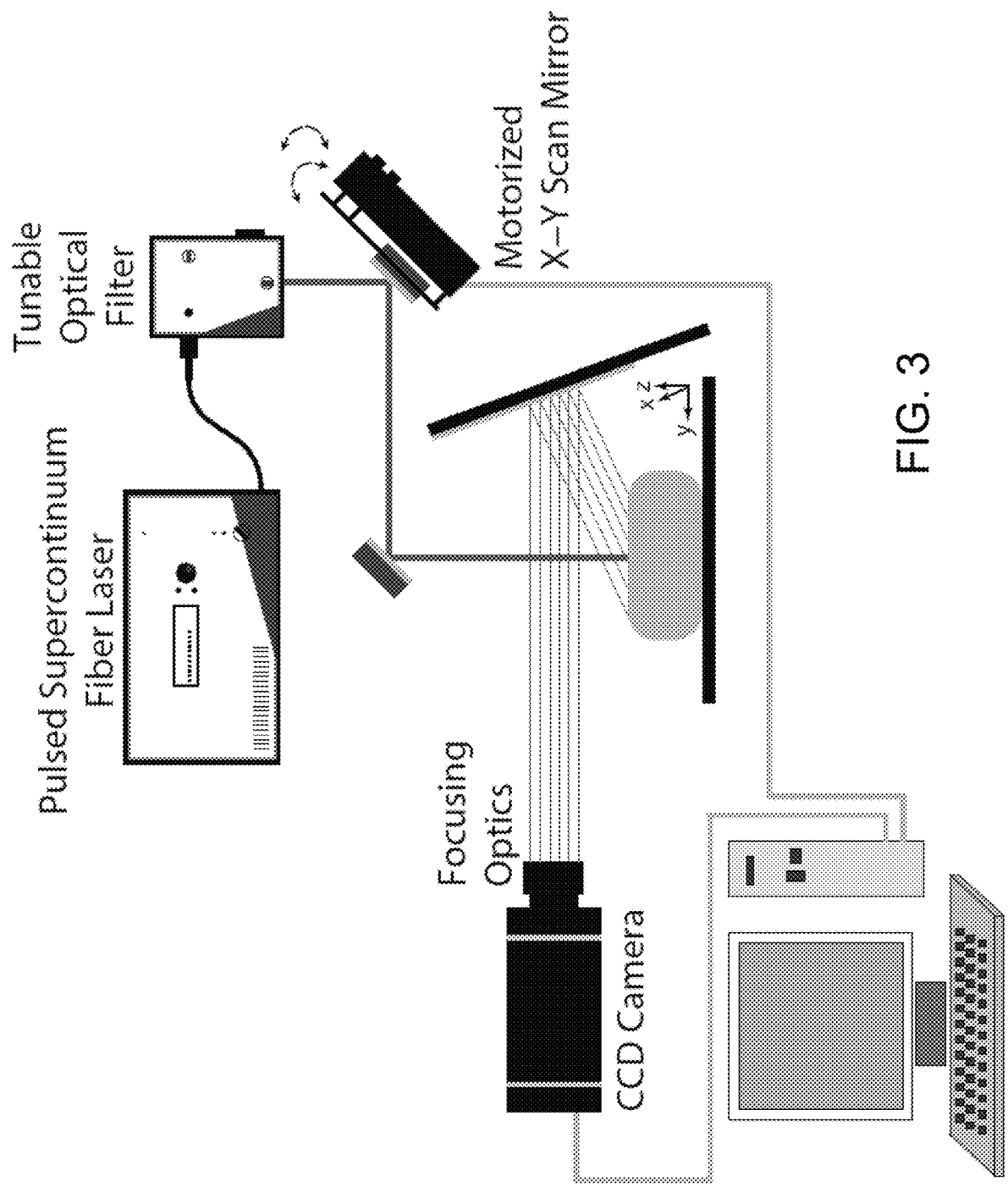
FIG. 3 schematically represents a nonlimiting diffuse optical imaging (DOI) experiment setup that was used in experiments to measure scattered light reflected from phantoms of the type depicted in FIG. 2(b).

Scattered light at 633 nm reflected from the mouth phantom was measured using a DOI experiment setup shown in FIG. 3. For high signal levels, Quasi-CW data (laser repetition rate 20 MHz, camera exposure time 25 ms) was detected using an EXR-20 pulsed supercontinuum fiber laser and VARIA tunable optical filter (both NKT Photonics) that emitted light centered at 633 nm with a 10 nm bandwidth. The scattered light was detected by a CCD camera (Roper PIMAX) that allowed for more measurements compared to a fiber-based system and enabled automation of the data capture and repeated measurements with the same source location. A laser line scanner was used to measure the surface topography and project the camera pixels (detectors) to the phantom's surface for the reconstruction. A motorized X-Y scan mirror (Zaber) was used to control the source location.

Two measurement sets were acquired, one with sources and detectors in the vicinity of the left absorption inhomogeneity and the other with sources and detectors in the vicinity of the right absorption inhomogeneity of the phantom of FIG. 2(b). The two measurement sets were used to localize the left and right arteries, respectively. A link list was used to exclude source-detector pairs with $r_{sd} < 10l^*$, where $l^* = 3D_o$, in order to minimize the contribution of the ballistic light. The left measurement set contained $N_L = 473$ measurements using seven sources and eighty detectors, and the right measurement set contained $N_R = 407$ measurements using seven sources and sixty detectors. The speed of the algorithm was linearly dependent on the number of measurements, because Eq. (10) and Eq. (11) must be calculated for each source-detector pair. The number of detectors could be minimized using a sensitivity analysis.

Both the left and right measurement data sets were calibrated component by component in order to account for the nonlinear source and detector coupling to the scattering medium. Data $y_n^{base}$ where n is the data index, was captured from the mouth phantom before the India ink and water were added. Then, the left and right uncalibrated measurement sets were calibrated according to $$y_n = y_n^{uncal}\left[\frac{y_n^{syn}}{y_n^{base}}\right], \quad (12)$$

where $y_n^{uncal}$ are uncalibrated data from either the left or right measurement set and $y_n^{syn}$ are corresponding simulated data (in this case equal to $y_o$). For a simple geometry, $$\left[\frac{y_n^{syn}}{y_n^{base}}\right]$$

in Eq. (12) may be approximately constant for each n. In this case, the calibration becomes $y_n = y_n^{uncal}\beta$, where $\beta$ is a constant that can be absorbed into $\Delta\mu_a$ in Eq. (9), removing the need for measuring $y_n^{base}$. However, it was found that calibration using Eq. (12) was necessary for localization in the phantom of FIG. 2(b). In the clinic, data from the phantom in FIG. 2(b) could be captured a priori and used for the calibration.

Figure 4:
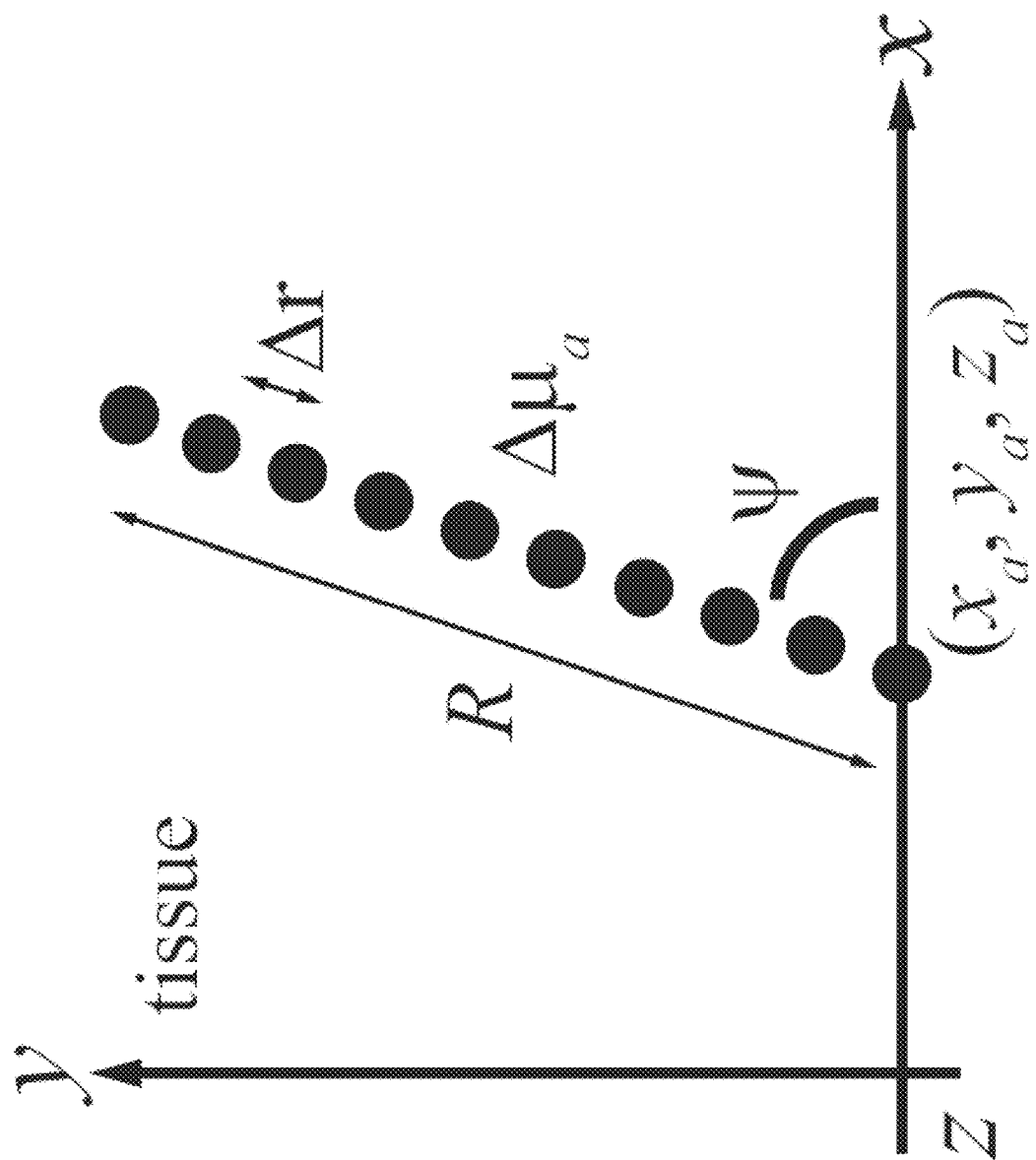
FIG. 4 is a plot that represents a nonlimiting constrained geometry for the localization of an absorbing line source represented by L=10 point absorbers (●).
Figure 5B:
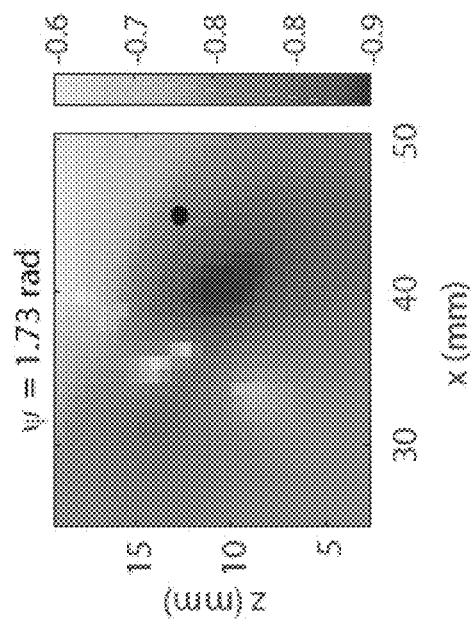
FIGS. 5(a) through 5(d) are images representing localizations using data captured above the left and right absorption inhomogeneities in the printed phantom of FIG. 2(b).
Figure 5A:
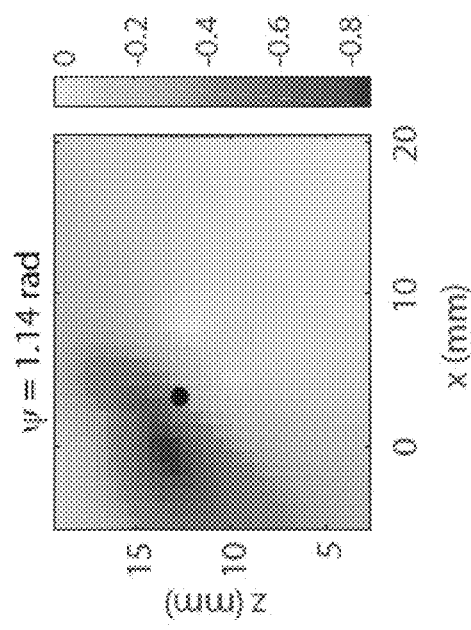
Figure 5D:
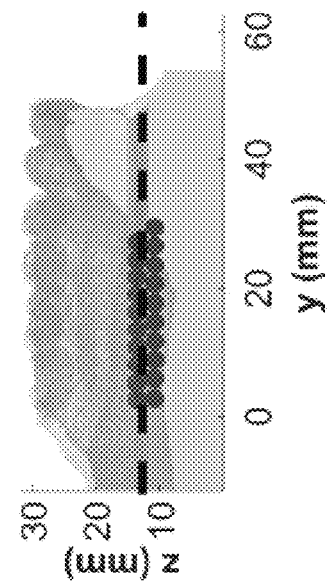
Figure 5C:
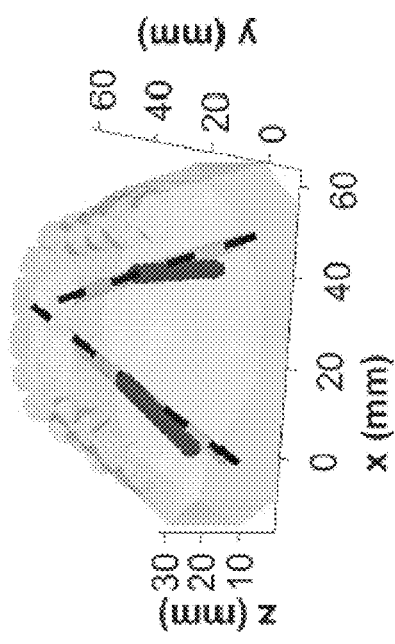

In order to localize the absorption inhomogeneities in the mouth phantom, the problem was constrained to the localization of absorbing line sources. Each line source was represented by L=10 point absorbers (●) and was characterized by its starting position $(x_a, y_a, z_a)$, its azimuth angle $\psi$, and a line of length R, as shown in FIG. 4. The positions $r_{a_l}$ of the point absorbers (●) are separated by $\Delta r$ along the length R starting at $(x_a, y_a, z_a)$. The problem was further constrained by selecting $y_a=0$ and R=30 mm, and using the left and right calibrated data sets to localize the left and right absorbing line sources, respectively. Specifically, Eq. (6) and then Eq. (7) were calculated for each $(x_a, y_a, \psi)$, in a region of interest for each absorbing line source. The position of each absorbing line source was then estimated using Eq. (8). The result of this localization procedure is shown in FIG. 5(a) through 5(d). FIG. 5(a) is a plot of Eq. (7) using the left data set and FIG. 5(b) is a plot of Eq. (7) using the right data set. The black dots represent the actual positions. For each $(x_a, y_a)$ shown, Eq. (7) was calculated for $\psi$ between 0 to $\pi/2$ (left) or $\pi/2$ to $\pi$ (right) radians. The plots show the xz plane for a fixed that contained the minimum cost. Note that as part of the constraint, $y_a=0$ was selected. FIGS. 5(c) and 5(d) are views that represent the localized absorption line sources (red dots) and the true locations (dashed black lines) plotted with the surface profile used to fabricate the mouth phantom. The minimum distance between the estimated and actual positions is about 0.8 mm, and the maximum distance is about 3.9 mm. This was a promising result given the approximations made in the forward model, the complicated geometry, and the high absorption of the simulated blood.

The localization in FIGS. 5(a) through 5(d) was based on a model constrained to an absorbing line source, but the constraint could be relaxed or modified to extract the more complicated vascular structure of the GPA in a real patient. Alternatively, point absorbers within the vascular structure could be localized individually, for example, by using a borescope.

Figure 6B:
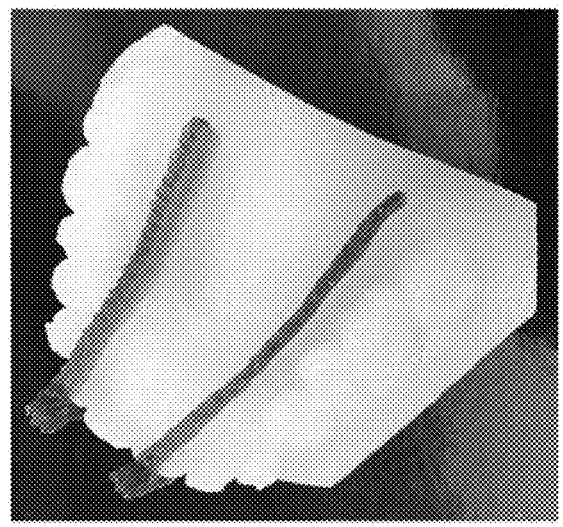
FIG. 6(a) is a schematic representation of a surgical guide device and FIG. 6(b) is an image showing a 3D printed surgical guide device intended to protect the greater palatine artery (GPA) of a human patient during a surgical procedure.
Figure 6A:
Figure 7:
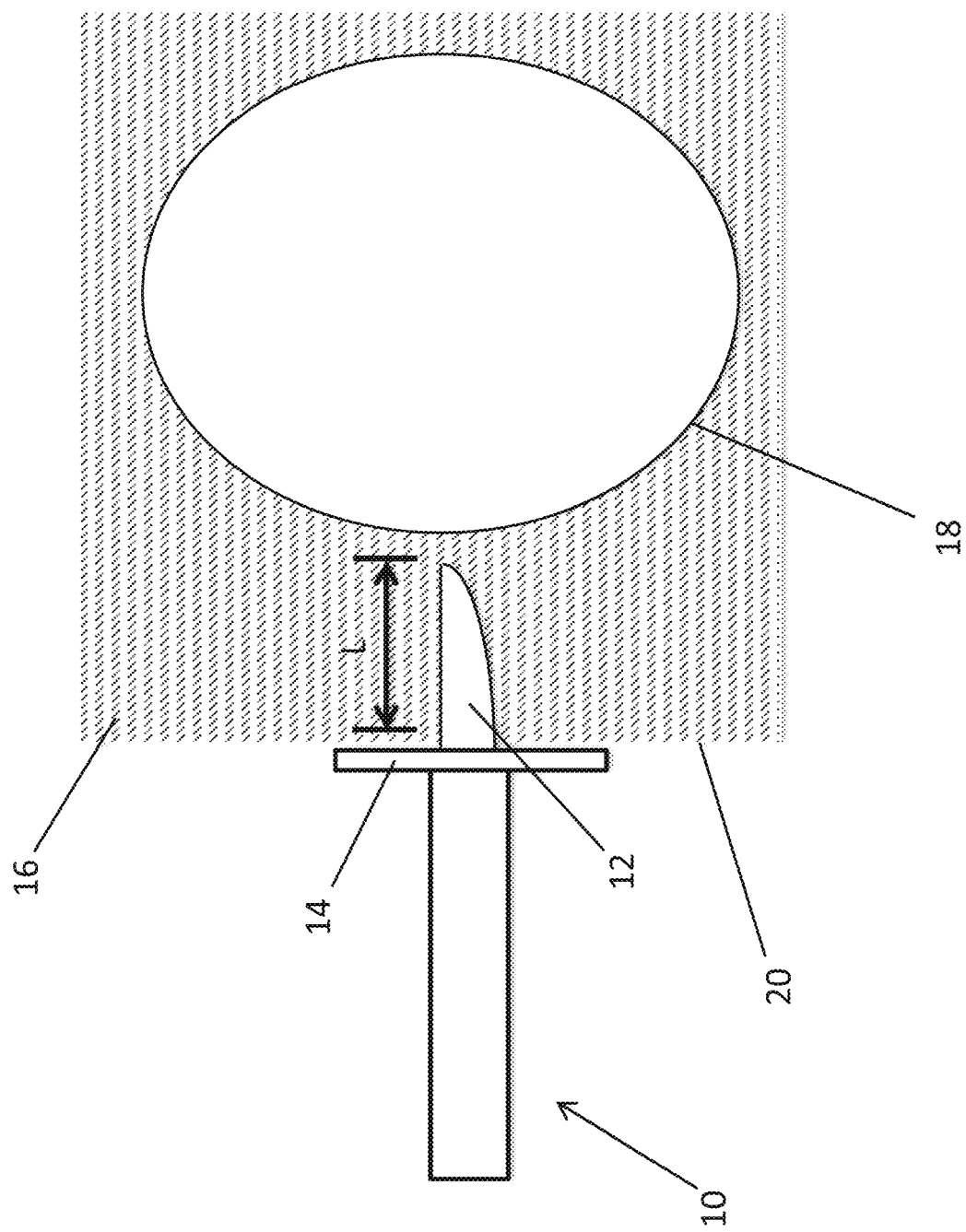
FIG. 7 is a schematic representation of a surgical tool that is designed using the optical imaging methods described herein to not damage a major blood vessel, such as the GPA.

Surgical guides can improve the success rate of surgery by transferring anatomical information to the operating theater. The data extracted using localization can be used to fabricate a surgical guide, for example, the pair of devices schematically represented in FIG. 6(a). This schematic was used to 3D print the surgical guide devices in FIG. 6(b). The blue lines in FIG. 6(a) are the estimated locations of the absorption line sources, and the dark blue/black isoimage represent the surgical guide devices. The isoimage was formed by projecting the blue lines to the phantom surface and selecting points on the surface less than the radial distance of the GPA away from the projected line. Additional points were added in the +z direction above these points to increase the thickness, and the resulting surface profile was converted into a stereolithography (STL) file, which was used to 3D print the surgical guide devices of FIG. 6(b). FIG. 6(b) shows each of the 3D printed surgical guide devices placed on the mouth phantom of FIG. 2(b). FIG. 6(b) shows that when the surgical guide devices are secured in the mouth, each GPA in the roof (hard palate) of the mouth phantom is occluded by an elongate body of each device so that a surgeon does not accidentally cut the GPA or the GPN associated therewith. The surgical guide device is capable of assisting with oral surgery by providing information on the location of the GPA and obstructing its location so that it and the GPN cannot or are less likely to be damaged. Preferably, the device is configured to be fastened in the mouth of a patient, such as through a clip or bonding material. It is foreseeable and within the scope of the invention that the location information may be used to produce other types of devices such as, but not limited to, custom surgical tools configured to limit the insertion or cutting depth of the tool during oral surgery such that it is less likely that the GPA will be cut or damaged. FIG. 7 schematically represents a nonlimiting example of such a tool 10 as comprising a knife 12 and guard 14, with the knife 12 penetrating tissue 16 to a depth that is short of a vessel 18 beneath the surface 20 of the tissue 16. For example, as shown schematically in FIG. 7, the length "L" of the knife 12 extending beyond the guard 14 is less than the depth of the vessel 18 beneath the surface 20 so that tissue can be harvested without damaging the vessel 18. Such a tool 10 could be fabricated quickly and uniquely for an individual patient using a 3D printer.

In view of the above, a DOI method for fast 3D localization of obscured absorption inhomogeneities is disclosed. The inhomogeneities are treated as a superposition of point absorbers with locations that can be constrained using prior information in order to reduce the computational burden. It is possible to localize absorbing line inhomogeneities within a highly scattering 3D printed mouth phantom from calibrated experimental data, which has relevance for oral surgery. Furthermore, the position information can be used to fabricate a surgical guide device using 3D printing to protect the GPA during surgery. In principle, the method could be employed in clinics using a bright light source and a camera or small probe. Images of the arteries could be viewed in real time, and a custom surgical guide device could be fabricated for a return visit. It is possible to localize lesions in addition to blood vessels, and to configure the surgical guide device to reduce complications. The specificity of the localization could be improved with topical fluorescence or absorption contrast agents. The method may also be useful for identifying operative and postoperative bleeding. Additionally, because the localization technique disclosed above provides for more precise locating of the GPA, its use can potentially enable more donor tissue to be harvested during surgical procedures that involve harvesting of soft tissue from the hard palate. Such a capability can potentially limit the need for follow-up surgery, for example, in cases where multiple teeth need gingival grafting.

While the invention has been described in terms of particular embodiments and investigations, it should be apparent that alternatives could be adopted by one skilled in the art. For example, the imaging system and surgical guide device could differ in appearance and construction from the embodiments described herein and shown in the drawings, functions of certain components could be performed by components of different construction but capable of a similar (though not necessarily equivalent) function, and various materials could be used in the fabrication of the surgical guide device and/or its components. Furthermore, alternative models and algorithm could be used to interpret the detected light. As such, it should be understood that the above detailed description is intended to describe the particular embodiments represented in the drawings and certain but not necessarily all features and aspects thereof, and to identify certain but not necessarily all alternatives to the represented embodiments and described features and aspects. As a nonlimiting example, the invention encompasses additional or alternative embodiments in which one or more features or aspects of a particular embodiment could be eliminated or two or more features or aspects of different embodiments could be combined. Accordingly, it should be understood that the invention is not necessarily limited to any embodiment described herein or illustrated in the drawings, and the phraseology and terminology employed above are for the purpose of describing the illustrated embodiments and investigations and do not necessarily serve as limitations to the scope of the invention. Therefore, the scope of the invention is to be limited only by the following claims.

The invention claimed is:

1. A method of locating a blood vessel in tissue, the method comprising:
   imaging the tissue via an optical imaging process that measures light that travels through the tissue; and then
   determining a location of the blood vessel in the tissue based on a difference in at least one of absorption and scattering of the light between the tissue and the blood vessel;
   wherein the tissue is in a human mouth, the blood vessel is a greater palatine artery (GPA) in a hard palate of the human mouth, and the method further comprises performing surgery and avoiding the GPA.

2. The method of claim 1, wherein the surgery comprises harvesting soft tissue from the hard palate while avoiding the GPA.

3. The method of claim 1, wherein the surgery comprises removing a soft tissue lesion.

4. The method of claim 1, further comprising:
   producing a surgical guide device based on a location of the GPA; and
   placing the surgical guide device on the tissue; and
   performing the surgery on the tissue while using the surgical guide device to mask the GPA during the surgery.

5. The method of claim 4, the method further comprising removing a soft tissue lesion during the surgery, and the surgical guide device serves to localize the surgery to facilitate the removal of the soft tissue lesion during the surgery.

6. The method of claim 1, wherein the surgery on the tissue is performed with a tool comprising a knife and a guard, the knife having a length extending beyond the guard, the guard limiting a cutting depth of the knife during the surgery.

7. The method of claim 4, wherein the surgery comprises harvesting soft tissue from the hard palate while avoiding the GPA.

8. The method of claim 1, further comprising:
   producing a surgical guide device based on a location of the GPA; and
   performing the surgery on the hard palate while using the surgical guide device to mask the GPA during the surgery.

9. The method of claim 8, further comprising placing the surgical guide device on the hard palate to mask the GPA during the surgery.

10. The method of claim 8, wherein the surgery on the hard palate is performed with a tool comprising a knife and a guard, the knife having a length extending beyond the guard, the guard limiting a cutting depth of the knife during the surgery.

11. The method of claim 1, further comprising using one or more topical fluorescence or absorption contrast agents that improve a specificity of the optical imaging process.

12. A method comprising:
   performing surgery on a body part of a living body;
   imaging the body part via an optical imaging process that measures light that travels through the body part; and then
   determining a location of operative or postoperative bleeding in the body part based on a difference in at least one of absorption and scattering of the light between blood and surrounding soft tissue in the body part;
   wherein the body part is a hard palate in a human mouth, and the bleeding is from a greater palatine artery (GPA) in the hard palate.

* * * * *